(12) United States Patent
Kugler et al.

(10) Patent No.: US 6,454,690 B2
(45) Date of Patent: Sep. 24, 2002

(54) METHOD AND APPARATUS FOR FORMING AN APERTURED PAD

(75) Inventors: Joseph Michael Kugler, Greenville, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 109 days.

(21) Appl. No.: 09/772,740

(22) Filed: Jan. 30, 2001

Related U.S. Application Data

(62) Division of application No. 09/272,119, filed on Mar. 19, 1999, now Pat. No. 6,220,999.

(51) Int. Cl.$^7$ ............................................... B31B 1/80
(52) U.S. Cl. ..................... 493/256; 493/257; 493/361
(58) Field of Search ................................ 493/256, 257, 493/267, 340, 344, 361, 370, 464, 960, 967; 604/378, 381

(56) References Cited

U.S. PATENT DOCUMENTS

| | | | |
|---|---|---|---|
| 3,371,667 A | 3/1968 | Morse | 128/290 |
| 3,431,911 A | 3/1969 | Meisel, Jr. | 128/287 |
| 3,441,023 A | 4/1969 | Rijssenbeek | 128/287 |
| 3,563,243 A | 2/1971 | Lindquist | 128/287 |
| 3,592,194 A | 7/1971 | Duncan | 128/287 |
| 3,744,494 A | 7/1973 | Marsan | 128/287 |
| 3,805,790 A | 4/1974 | Kaczmarzyk et al. | 128/290 R |

(List continued on next page.)

FOREIGN PATENT DOCUMENTS

| | | |
|---|---|---|
| EP | 0 343 941 A2 | 11/1989 |
| EP | 0 774 242 A1 | 5/1997 |

(List continued on next page.)

OTHER PUBLICATIONS

Federal Test Method Standard (FTMS) No. 191A, Method 5450, "Permeability To Air; Cloth; Calibrated Orifice Method," Jul. 20, 1978, 5 pages.

Federal Test Method Standard (FTMS) No. 191A, Method 5514, "Water Resistance of Cloth; Low Range, Hydrostatic Pressure Method," Jul. 20, 1978, 3 pages.

(List continued on next page.)

*Primary Examiner*—Eugene Kim
(74) *Attorney, Agent, or Firm*—Alyssa A. Dudkowski; Jeffrey B. Curtin

(57) ABSTRACT

An apparatus and method for manufacturing a pad wherein a rotatable forming screen which has a generally cylindrical surface and at least one outwardly projecting nob is employed. The nob is positioned on the forming screen whereby the nob is circumscribed by the material, e.g., cellulosic fluff, deposited on the forming screen to form the pad. The pad is transferred from the forming screen to a moveable transfer surface. The transfer surface may be either flat or round and moves at a velocity which is at least as great as the velocity of the forming screen. The nob located on the forming screen includes a thrust surface disposed on a trailing edge of the nob. The thrust surface imparts a compressive force on the pad during the release of the pad from the forming screen. The compressive force is at least partially directed towards the transfer surface and thereby assists in the release and transfer of the pad. A vacuum may also be used to attract the pad to the transfer surface. When the transfer surface is a cylindrical surface, the forming screen may have a diameter which is smaller than, substantially equivalent to, or greater than the diameter of the transfer surface. The nobs disposed on the forming screen can have many different shapes and, for example, may define a frustum. The sidewalls of the nob may taper inwardly by about 5 degrees. Threaded fasteners may be utilized to make the nobs reattachable and exchangeable.

26 Claims, 7 Drawing Sheets

U.S. PATENT DOCUMENTS

| | | | | |
|---|---|---|---|---|
| 3,889,679 A | 6/1975 | Taylor | | 128/287 |
| 3,890,973 A | 6/1975 | Davis et al. | | 128/286 |
| 3,916,900 A | 11/1975 | Breyer et al. | | 128/287 |
| 3,927,673 A | 12/1975 | Taylor | | 128/287 |
| 3,945,386 A | 3/1976 | Anczurowski et al. | | 128/287 |
| 4,055,184 A | 10/1977 | Karami | | 128/287 |
| 4,276,338 A | 6/1981 | Ludwa et al. | | 428/137 |
| 4,306,559 A | 12/1981 | Nishizawa et al. | | 128/287 |
| 4,389,211 A | 6/1983 | Lenaghan | | 604/383 |
| 4,413,996 A | 11/1983 | Taylor | | 604/382 |
| 4,560,372 A | 12/1985 | Pieniak | | 604/369 |
| 4,568,341 A | 2/1986 | Mitchell et al. | | 604/368 |
| 4,592,751 A | 6/1986 | Gegelys | | 604/368 |
| 4,596,567 A | 6/1986 | Iskra | | 604/368 |
| 4,608,292 A | 8/1986 | Lassen | | 428/131 |
| 4,624,666 A | 11/1986 | DeRossett et al. | | 604/366 |
| 4,634,440 A | 1/1987 | Widlund et al. | | 604/383 |
| 4,674,966 A | 6/1987 | Johnson et al. | | 425/82.1 |
| 4,676,784 A | 6/1987 | Erdman et al. | | 604/368 |
| 4,676,786 A | 6/1987 | Nishino | | 604/378 |
| 4,704,112 A | 11/1987 | Suzuki et al. | | 604/378 |
| 4,731,065 A | 3/1988 | Yamada | | |
| 4,735,624 A | 4/1988 | Mazars | | |
| 4,761,258 A | 8/1988 | Enloe | | |
| 4,762,521 A | 8/1988 | Roessler et al. | | |
| 4,781,710 A | 11/1988 | Megison et al. | | |
| 4,787,896 A | 11/1988 | Houghton et al. | | |
| 4,798,603 A | 1/1989 | Meyer et al. | | |
| 4,840,692 A | 6/1989 | Kamstrup-Larsen | | |
| 4,892,535 A | 1/1990 | Bjornberg et al. | | |
| 4,908,026 A | 3/1990 | Sukiennik et al. | | |
| 4,988,345 A | 1/1991 | Reising | | |
| 4,990,147 A | 2/1991 | Freeland | | |
| 5,030,229 A | 7/1991 | Yang | | |
| 5,061,260 A | 10/1991 | Callahan et al. | | |
| 5,062,840 A | 11/1991 | Holt et al. | | |
| 5,078,710 A | 1/1992 | Suda et al. | | |
| 5,137,525 A | 8/1992 | Glassman | | |
| 5,141,794 A | 8/1992 | Arroyo | | |
| 5,171,236 A | 12/1992 | Dreier et al. | | |
| 5,171,238 A | 12/1992 | Kajander | | |
| 5,176,668 A | 1/1993 | Bernardin | | |
| 5,176,672 A | 1/1993 | Bruemmer et al. | | |
| 5,192,606 A | 3/1993 | Proxmire et al. | | |
| 5,226,991 A | 7/1993 | Svaighert | | |
| 5,242,435 A | 9/1993 | Murji et al. | | |
| 5,263,948 A | 11/1993 | Karami et al. | | |
| 5,279,854 A | 1/1994 | Kendall et al. | | |
| 5,294,478 A | 3/1994 | Wanek et al. | | |
| 5,300,053 A | 4/1994 | Genaro | | |
| 5,304,161 A | 4/1994 | Noel et al. | | |
| 5,306,266 A | 4/1994 | Freeland | | |
| 5,324,278 A | 6/1994 | Visscher et al. | | |
| 5,330,457 A | 7/1994 | Cohen | | |
| 5,334,177 A | 8/1994 | Cohen | | |
| 5,356,405 A | 10/1994 | Thompson et al. | | |
| 5,364,382 A | 11/1994 | Latimer et al. | | |
| 5,366,451 A | 11/1994 | Levesque | | |
| 5,366,452 A | 11/1994 | Widlund et al. | | |
| 5,383,870 A | 1/1995 | Takai et al. | | |
| 5,387,209 A | 2/1995 | Yamamoto et al. | | |
| 5,391,160 A | 2/1995 | Runeman et al. | | |
| 5,397,316 A | 3/1995 | LaVon et al. | | |
| 5,429,629 A | 7/1995 | Latimer et al. | | |
| 5,439,458 A | 8/1995 | Noel et al. | | |
| 5,451,442 A | 9/1995 | Pieniak et al. | | |
| 5,462,541 A | 10/1995 | Bruemmer et al. | | |
| 5,482,765 A | 1/1996 | Bradley et al. | | |
| 5,486,166 A | 1/1996 | Bishop et al. | | |
| 5,490,846 A | 2/1996 | Ellis et al. | | |
| 5,494,622 A | 2/1996 | Heath et al. | | |
| 5,500,270 A | 3/1996 | Langdon et al. | | |
| 5,505,719 A | 4/1996 | Cohen et al. | | |
| 5,505,720 A | 4/1996 | Walters et al. | | |
| 5,509,915 A | 4/1996 | Hanson et al. | | |
| 5,514,104 A | 5/1996 | Cole et al. | | |
| 5,514,105 A | 5/1996 | Goodman, Jr. et al. | | |
| 5,514,120 A | 5/1996 | Johnston et al. | | |
| 5,520,674 A | 5/1996 | Lavon et al. | | |
| 5,533,991 A | 7/1996 | Kirby et al. | | |
| 5,536,264 A | 7/1996 | Hsueh et al. | | |
| 5,549,775 A | 8/1996 | Odorzynski | | |
| 5,558,655 A | 9/1996 | Jezzi et al. | | |
| 5,558,658 A | 9/1996 | Menard et al. | | |
| 5,562,649 A | 10/1996 | Chauvette et al. | | |
| 5,562,650 A | 10/1996 | Everett et al. | | |
| 5,569,226 A | 10/1996 | Cohen et al. | | |
| 5,571,096 A | 11/1996 | Dobrin et al. | | |
| 5,591,148 A | 1/1997 | McFall et al. | | |
| 5,593,399 A | 1/1997 | Tanzer et al. | | |
| 5,603,707 A | 2/1997 | Trombetta et al. | | |
| 5,611,790 A | 3/1997 | Osborn, III et al. | | |
| 5,613,962 A | 3/1997 | Kenmochi et al. | | |
| 5,614,283 A | 3/1997 | Potnis et al. | | |
| 5,624,422 A | 4/1997 | Allen | | |
| 5,628,737 A | 5/1997 | Dobrin et al. | | |
| 5,637,105 A | 6/1997 | Tanaka et al. | | |
| 5,641,441 A | 6/1997 | Yang | | |
| 5,643,238 A | 7/1997 | Baker | | |
| 5,643,239 A | 7/1997 | Bodford et al. | | |
| 5,643,240 A | 7/1997 | Jackson et al. | | |
| 5,653,702 A | 8/1997 | Brohammer et al. | | |
| 5,662,633 A | 9/1997 | Doak et al. | | |
| 5,662,634 A | 9/1997 | Yamamoto et al. | | |
| 5,669,895 A | 9/1997 | Murakami et al. | | |
| 5,669,896 A | 9/1997 | Kielpikowski | | |
| 5,674,212 A | 10/1997 | Osborn, III et al. | | |
| 5,674,214 A | 10/1997 | Visscher et al. | | |
| 5,677,028 A | 10/1997 | Ravella | | |
| 5,683,375 A | 11/1997 | Osborn, III et al. | | |
| 5,695,487 A | 12/1997 | Cohen et al. | | |
| 5,702,382 A | 12/1997 | Osborn, III et al. | | |
| 5,713,881 A | 2/1998 | Rezai et al. | | |
| 5,785,697 A | 7/1998 | Trombetta et al. | | |
| 5,788,684 A | 8/1998 | Abuto et al. | | |
| 5,810,798 A | 9/1998 | Finch et al. | | |
| 5,846,231 A | 12/1998 | Fujioka et al. | | |
| 6,220,999 B1 * | 4/2001 | Kugler et al. | | |

FOREIGN PATENT DOCUMENTS

| | | |
|---|---|---|
| GB | 2 296 438 A | 7/1996 |
| WO | WO 90/05511 A1 | 5/1990 |
| WO | WO 91/00719 A1 | 1/1991 |
| WO | WO 91/09582 A1 | 7/1991 |
| WO | WO 91/09583 A1 | 7/1991 |
| WO | WO 92/11830 A2 | 7/1992 |
| WO | WO 95/05139 A1 | 2/1995 |
| WO | WO 95/13042 A1 | 5/1995 |
| WO | WO 95/17869 A1 | 7/1995 |
| WO | WO 95/17870 A1 | 7/1995 |
| WO | WO 96/00545 A1 | 1/1996 |
| WO | WO 96/03947 A1 | 2/1996 |
| WO | WO 96/12457 A1 | 5/1996 |
| WO | WO 96/15748 A3 | 5/1996 |
| WO | WO 96/20668 A1 | 7/1996 |
| WO | WO 96/20669 A1 | 7/1996 |
| WO | WO 96/20670 A1 | 7/1996 |
| WO | WO 96/20671 A1 | 7/1996 |
| WO | WO 96/21409 A3 | 7/1996 |
| WO | WO 96/34589 A2 | 11/1996 |
| WO | WO 97/11660 A1 | 4/1997 |

| | | |
|---|---|---|
| WO | WO 97/14385 A1 | 4/1997 |
| WO | WO 97/17923 A1 | 5/1997 |
| WO | WO 97/24097 A1 | 7/1997 |
| WO | WO 97/33544 A1 | 9/1997 |
| WO | WO 97/34557 A1 | 9/1997 |
| WO | WO 97/34558 A1 | 9/1997 |
| WO | WO 97/34559 A1 | 9/1997 |
| WO | WO 97/36562 A1 | 10/1997 |
| WO | WO 97/40800 A1 | 11/1997 |
| WO | WO 97/40801 A1 | 11/1997 |
| WO | WO 98/00081 A1 | 1/1998 |
| WO | WO 98/19861 A2 | 5/1998 |
| WO | WO 98/22067 A1 | 5/1998 |
| WO | WO 98/26741 A1 | 6/1998 |
| WO | WO 98/58607 A1 | 12/1998 |
| WO | WO 98/58608 A1 | 12/1998 |
| WO | WO 98/58609 A1 | 12/1998 |
| WO | WO 98/58610 A1 | 12/1998 |
| WO | WO 98/58611 A1 | 12/1998 |
| WO | WO 98/58615 A1 | 12/1998 |

OTHER PUBLICATIONS

Berglund, Larry G. and Frank J. Akin, "Measurement Of Air Exchange In Diapers By Tracer Gas Methods," Tappi Journal, vol. 80, No. 9, Sep. 1997, pp. 173–178.

Williamson, P. and A.M. Kligman, "A New Method For Quantitative Investigation of Cutaneous Bacteria," Journal of Investigative Dermatology, 45:498–503, 1965.

Patent Cooperation Treaty Search Report from the International Search Authority, International Application No. PCT/US 00/07324 dated Aug. 11, 2000.

* cited by examiner

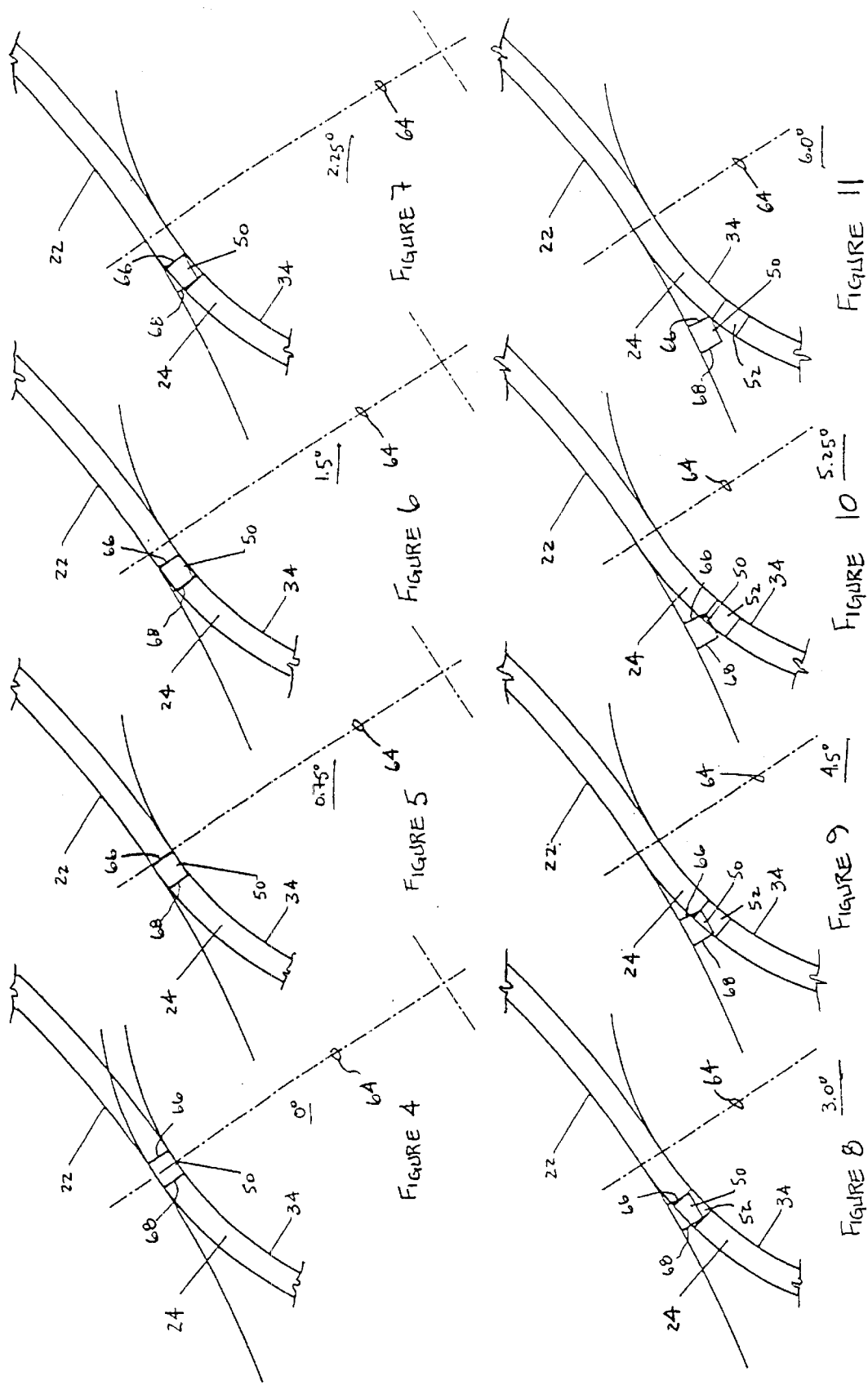

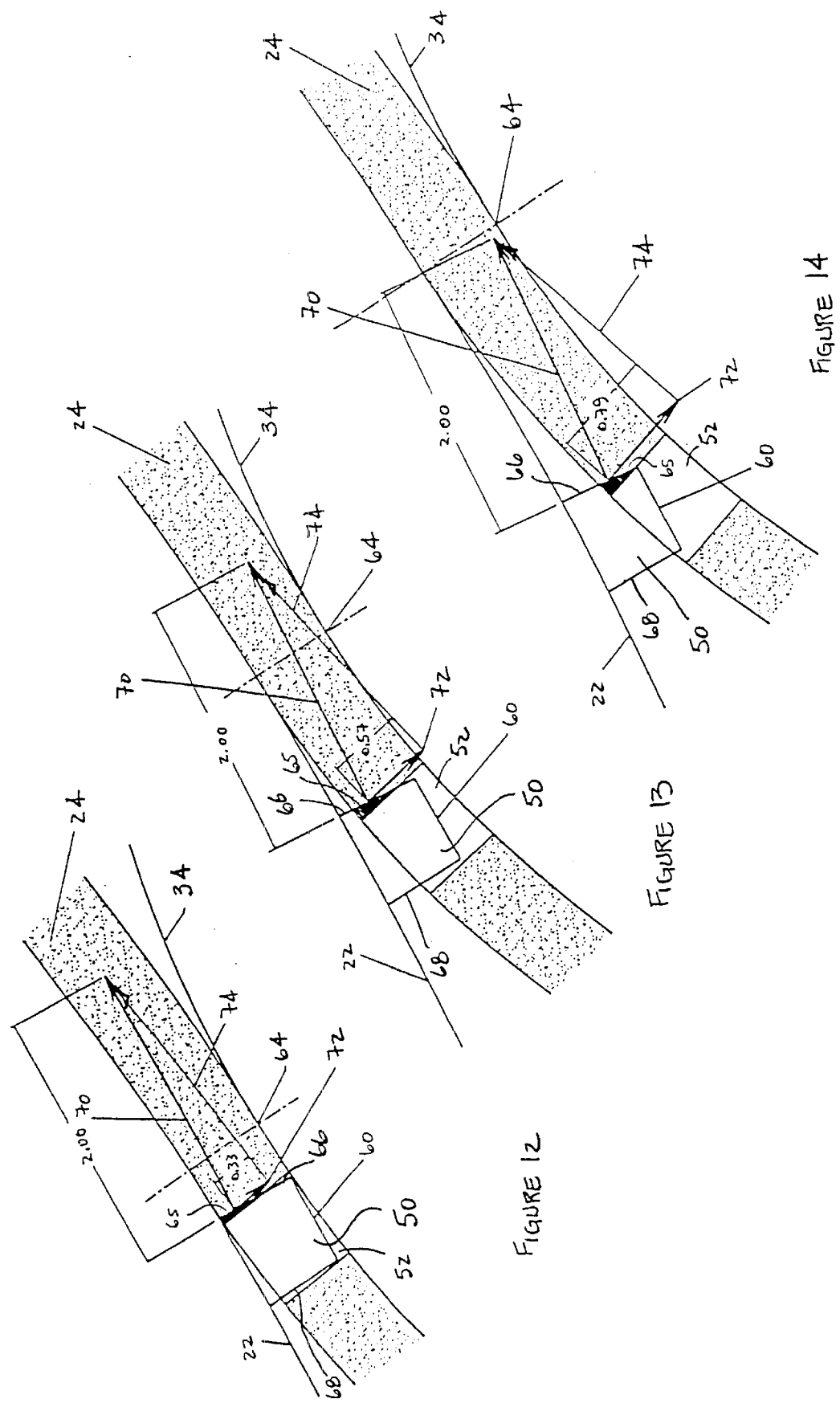

METHOD AND APPARATUS FOR FORMING AN APERTURED PAD

This application is a division of Ser. No. 09/272,119 filed on Mar. 19, 1999 now U.S. Pat. No. 6,220,999.

BACKGROUND OF THE INVENTION

The present invention relates to the apparatus and methods used to form apertured pads. More specifically, the present invention relates to apparatus and methods used to form absorbent apertured pads which may be used in such products as disposable diapers, training pants, incontinence garments, catamenial products and other absorbent articles.

Conventional absorbent pads often consist primarily of a cellulosic fluff or other fibrous material. Such absorbent pads may be used in the manufacture of products subject to surge loadings. The expected surge loadings may exceed the rapid intake capability of conventional absorbent pads. Apertures placed in the pads, however, can enhance the rapid intake capability of the pad. Such apertures may consist of empty voids or be filled with a material having different properties than the remainder of the pad.

Such apertures may be employed for purposes other than enhancing the rapid intake capability of the pad. For example, when the apertured pad is used in a disposable diaper, the apertures may provide additional void space for storing and receiving solid wastes or to provide space for the expansion of superabsorbent materials.

The conventional manufacture of apertured pads involves air laying a fluff pad on a forming drum. The pad is subsequently apertured in a separate cutting, calendering or similar procedure. U.S. Pat. No. 5,242,435 discloses, inter alia, the calendering and perfembossing of a cellulosic pulp fluff sheet. U.S. Pat. No. 5,785,697 discloses a different method of forming an apertured pad which involves, inter alia, the use of raised portions on a forming surface employed to form an absorbent composite web.

SUMMARY OF THE INVENTION

The present inventors have recognized difficulties and problems inherent in the prior art and in response thereto have developed an improved apparatus and method for forming an apertured pad.

In one aspect, the present invention provides an apparatus for manufacturing a pad wherein the apparatus comprises, i.e., includes but is not limited to, a rotatable forming screen which has a generally cylindrical surface and at least one outwardly projecting nob. The nob is located on the screen in a position whereby the nob is circumscribed by the forming screen. The forming screen is rotatable at a rate which defines a first tangential velocity of the screen. A material source is positioned adjacent the forming screen whereby a material layer may be air layered on the forming screen and the nob may be circumscribed by the material layer. The deposited material layer has a first surface in contact with the forming screen and an opposite second surface. A moveable transfer surface is engageable with the second surface of the material layer. The transfer surface is moveable in a direction which substantially corresponds to the movement of the material layer and at a second velocity which is at least as great as the first tangential velocity of the forming screen. The apparatus also includes a means for attracting the material layer to the transfer surface which may, in some embodiments, be a vacuum source disposed in operative communication with the transfer surface. The nob located on the forming screen includes a thrust surface disposed on a trailing edge of the nob. The thrust surface imparts a compressive force on the material layer at the point where the material layer is engageable with the transfer surface and as the forming screen and the transfer surface move at their respective first and second velocities. The compressive force exerted by the thrust surface of the nob includes a component vector which is directed towards the transfer surface.

In some embodiments of the apparatus, the velocity of the transfer surface may be 101, 102, 103, or a greater percentage of the tangential velocity of the forming screen at the transfer location.

In other embodiments of the apparatus, the transfer surface may be either a flat surface or a substantially cylindrical surface. In those embodiments wherein the transfer surface is a substantially cylindrical surface, the forming screen can have a radius which is less than, approximately equivalent to, or larger than the radius which defines the transfer surface. When the forming screen has a larger radius, the forming screen radius may be greater than twice or three times the magnitude of the transfer surface radius.

The nob disposed on the forming screen can have many different shapes. The nob may have sidewalls which incline inwardly by about 5° to form an angle of approximately 85° with the forming screen. Such nobs may have a shape which defines a frustum.

The apparatus may also include a plurality of nobs located on the forming screen. The nobs may also be reattachable to the screen as, for example, by using threaded fasteners to secure the nobs to the forming screen. The use of reattachable nobs allows the nobs on the forming screen to be exchanged in a relatively convenient manner.

The present invention also provides a method of forming an apertured pad. One such method includes providing a forming screen with at least one outwardly projecting nob and rotating the forming screen whereby the screen has a first tangential velocity. A pad is formed on the forming screen whereby the pad completely encircles the nob. The pad has a first surface in contact with the forming screen and an opposite second surface. A moving transfer surface is provided adjacent the second surface of the pad and is moved in a direction which substantially corresponds to the movement of the pad and at a velocity which is at least as great as the tangential velocity of the forming screen. The transfer surface is engaged with the second surface of the pad and the pad is transferred to the transfer surface. During the transfer of the pad, a trailing edge of the nob exerts a compressive force on the pad wherein the compressive force includes a component vector which is directed towards the transfer surface.

In some embodiments of the method, the velocity of the transfer surface may be 101, 102, 103, or greater percentage of the tangential velocity of the forming screen at the transfer location.

In other embodiments of the method, the transfer surface may be either a flat surface or a substantially cylindrical surface. In those embodiments wherein the transfer surface is a substantially cylindrical surface, the forming screen may have a radius which less than, substantially equivalent to, or greater than the transfer surface radius. When the forming screen has a larger radius, the forming screen radius may be greater than twice or three times the magnitude of the transfer surface radius.

A variety of differently shaped nobs may be used with the methods of the present invention. The nobs may have sidewalls which incline inwardly by about 5° to form an angle of approximately 85° with the forming screen. Such nobs may also have a shape which defines a frustum. A plurality of nobs may be used on the forming screen. The nobs may also be reattachable to the screen as, for example, by using threaded fasteners to secure the nobs to the forming screen. The use of reattachable nobs allows one or more of the nobs present on the forming screen to be exchanged for a different nob in a relatively convenient manner.

The apparatus and method of the present invention provide numerous advantages. The configuration and relative motion of the forming screen and transfer surface of the apparatus and method allow the trailing edge of the nob to exert a compressive force on the fluff pad which includes a component vector directed towards the transfer surface. That portion of the compressive force which is directed towards the transfer surface assists in the transfer of the pad to the transfer surface.

Furthermore, by having the trailing edge of the nob exert a compressive force on the pad, the leading edge of the nob will not exert a compressive force on the pad. If the leading edge of the nob were to exert a compressive force on the pad, there would be a significant possibility of the nob damaging or removing the pad material adjacent the leading edge of the nob. In contrast, the apparatus and methods of the present invention create an aperture with a relatively cleanly defined perimeter.

The apparatus and methods of the present invention also provide for the efficient manufacture of apertured pads. No post-formation cutting or calendering operation is required to form apertures in the pads of the present invention. Furthermore, the elimination of the post-formation cutting or calendering operation also eliminates the scrap and additional handling associated with such a post-formation aperturing process.

Another advantage of the present invention is that it may be implemented using reattachable nobs. When reattachable nobs are used, they may be easily exchanged for differently configured nobs. This ability allows the aperture size and geometry to be easily adjusted to optimize the performance of the pad.

BRIEF DESCRIPTION OF THE DRAWINGS

The invention will be more fully understood and further advantages will become apparent when reference is made to the following detailed description of the invention and the accompanying drawings, in which:

FIG. 4 is a side view of a forming drum and transfer roll wherein a nob on the transfer roll is located at the normal line which intersects the centers of both the forming drum and transfer roll;

FIG. 5 is a side view of the apparatus of FIG. 4 wherein the forming drum has rotated 0.75°;

FIG. 6 is a side view of the apparatus of FIG. 4 wherein the forming drum has rotated 1.50°;

FIG. 7 is a side view of the apparatus of FIG. 4 wherein the forming drum has rotated 2.25°;

FIG. 8 is a side view of the apparatus of FIG. 4 wherein the forming drum has rotated 3.00°;

FIG. 9 is a side view of the apparatus of FIG. 4 wherein the forming drum has rotated 4.50°;

FIG. 10 is a side view of the apparatus of FIG. 4 wherein the forming drum has rotated 5.25°;

FIG. 11 is a side view of the apparatus of FIG. 4 wherein the forming drum has rotated to 6.00°;

FIG. 12 is a side view of the apparatus of FIG. 4 wherein the forming drum has rotated 1.5° and which illustrates the compressive forces exerted by the nob;

FIG. 13 is a side view of the apparatus of FIG. 4 wherein the forming drum has rotated 3.0° and which illustrates the compressive forces exerted by the nob;

FIG. 14 is a side view of the apparatus of FIG. 4 wherein the forming drum has rotated 4.5° and which illustrates the compressive forces exerted by the nob;

Figure 1:
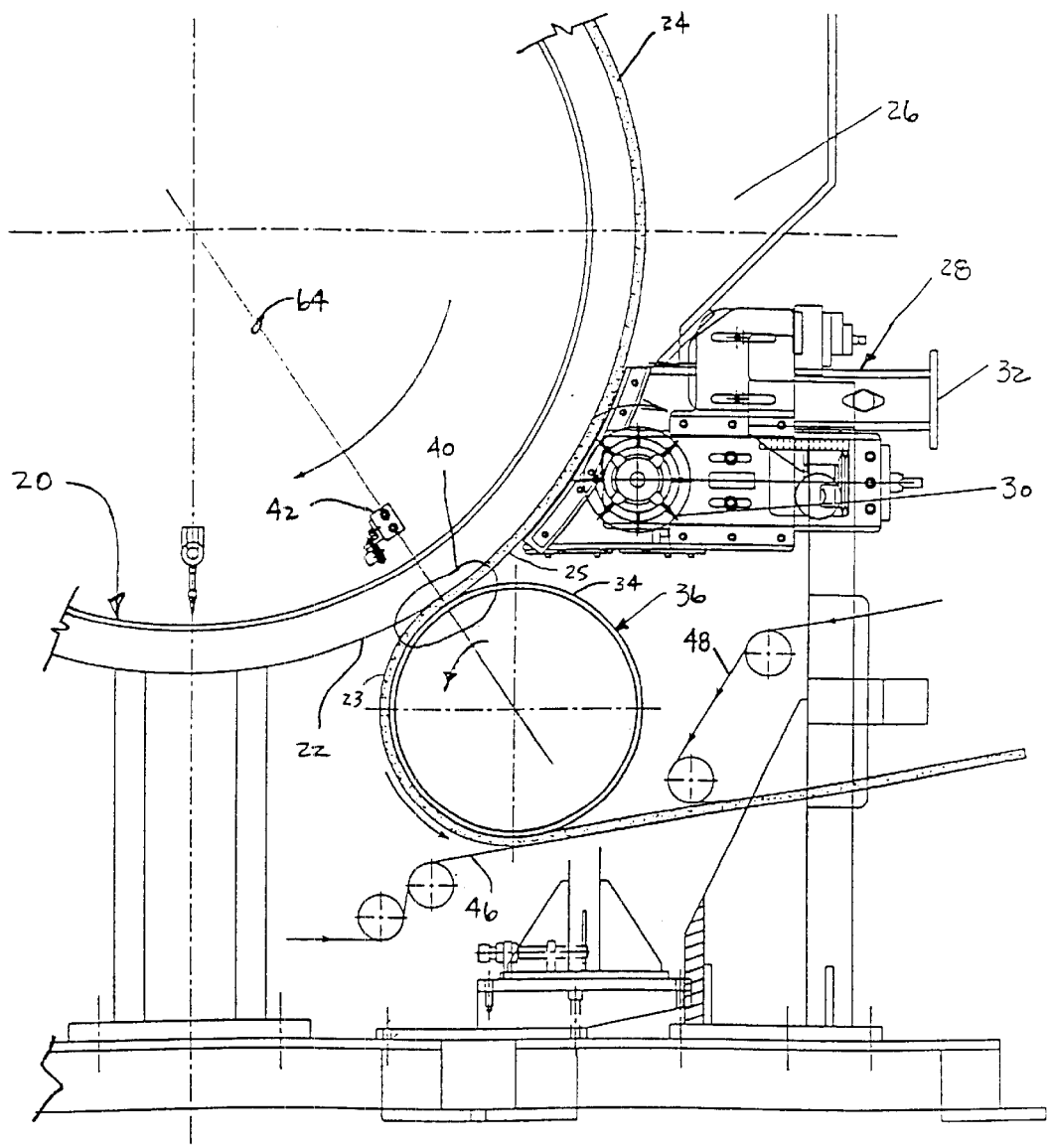
FIG. 1 is a partial side view of an apparatus in accordance with the present invention.

Corresponding reference characters indicate corresponding parts throughout the several views. The disclosed embodiments are set forth to illustrate and exemplify the invention. The disclosed embodiments are not intended to be an exhaustive illustration of the invention or to be construed as limiting the scope of the invention to the precise forms disclosed.

DETAILED DESCRIPTION OF THE INVENTION

An apparatus for forming an apertured pad is illustrated in FIG. 1. A portion of cylindrical forming drum 20 is shown in FIG. 1. A forming screen 22 defines the cylindrical surface of the forming drum 20. The forming screen 22 has openings therein which allow the passage of process air but which are small enough to prevent the passage of the material used to form the pad 24. The forming screen 22 also includes nobs 50 which both form apertures 52 within the pad 24 and assist in the release of the pad 24 from the forming drum 20. The nobs 50 are discussed in greater detail below.

The pad 24 is formed by depositing material on the forming screen within the forming chamber 26 in an air laying process. A variety of forming chambers are known in the art and provide a source of material adjacent the forming screen 22. A vacuum source operatively associated with the forming drum 20 removes air from the forming chamber 26 through the forming screen 22 and thereby deposits the material on the forming screen 22.

A wide variety of materials may be used with the present invention to form apertured pad 24. Oftentimes, pads 24 are used in consumer products intended for absorbing liquids or bodily excretions and the materials used to form such pads will generally include at least some absorbent materials. Such pads are often formed by a mixture of hydrophilic fibers and superabsorbent materials. Materials which may be used to form pad 24 include cellulosic pulp, cotton, rayon, and other natural or synthetic fibers. Superabsorbent materials may be mixed with these materials to enhance the absorbency of the pad. A fluff material derived from wood pulp is commonly used to form absorbent pads, and such fluff material may be employed with the apparatus illustrated in FIGS. 1 and 2. The detailed description which is presented herein discusses the present invention in terms of a pad 24 formed with such fluff material but alternative materials may also be employed with the present invention.

Prior to entering the forming chamber 26, compressed wood pulp may be pulverized in a hammermill or other fiberizing equipment to produce the fluff material. The use of hammermills and similar fiberizing equipment is well known in the art. The fluff material is then conveyed from the hammermill to the forming chamber 26. The fluff may also have additional materials added thereto, such as superabsorbent materials, either prior or subsequent to depositing the fluff material on the forming screen 22.

A scarfing unit 28 is not required, but may be advantageously positioned after the forming chamber 26 to remove excess fluff from the pad 24. The scarfing unit 28 includes a pin scarfing roll 30 and a removal air duct 32. The removal air duct 32 may be advantageously employed to recycle the removed material. For example, the duct 32 may transport the removed material to the hammermill or forming chamber 26 where the removed material may be reintroduced into the manufacturing process. Alternatively, the duct 32 may transport the material to a temporary storage chamber prior to reintroducing the material into the manufacturing process or be employed as a component in an alternative recycling or disposal method.

Figure 2:
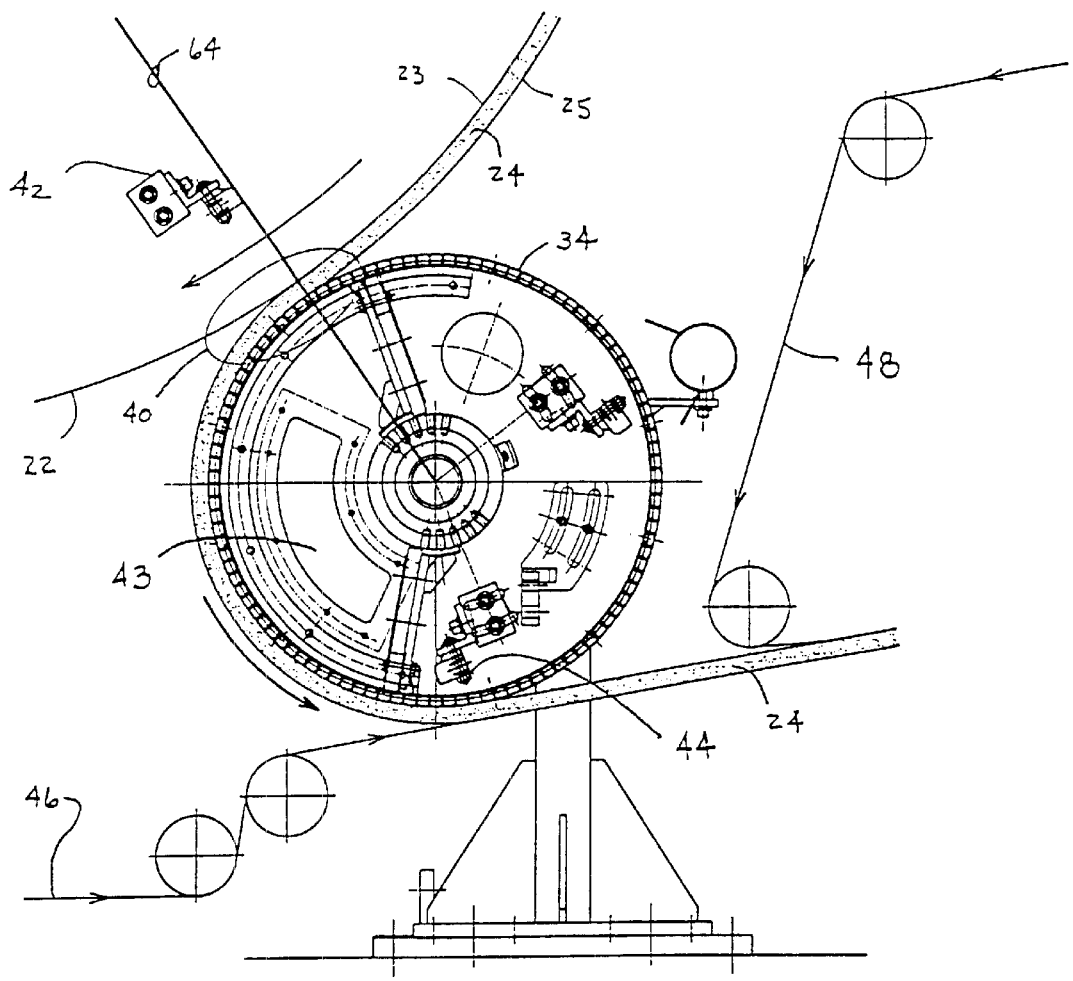
FIG. 2 is a partial side view of the apparatus of FIG. 1 with the operator side wall removed from the transfer roll.
Figure 15:
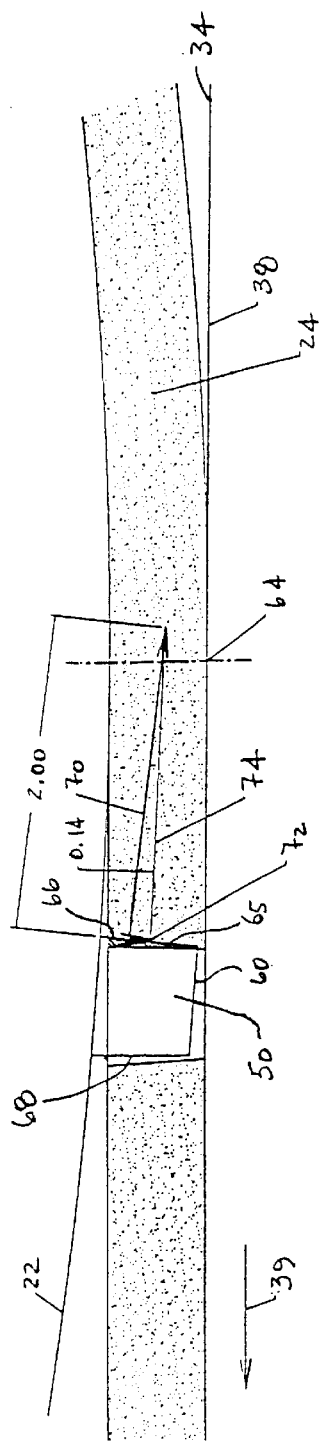
FIG. 15 is a side view of a forming drum and a flat conveyor wherein a nob on the forming drum has rotated 4° beyond a normal line located at the point where the forming drum is closest to the conveyor.
Figure 16:
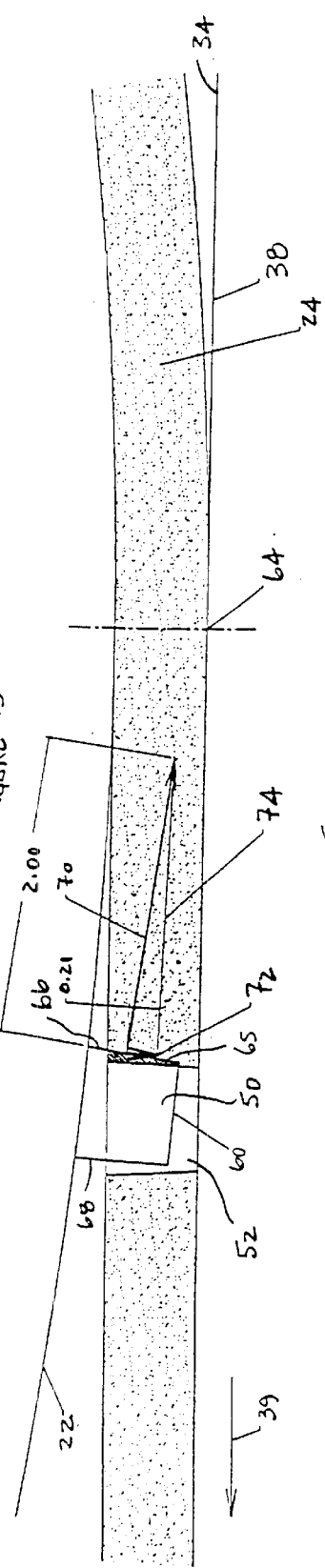
FIG. 16 is a side view of the apparatus of FIG. 15 wherein the forming nob has rotated to a point 6° beyond the normal line.
Figure 17:
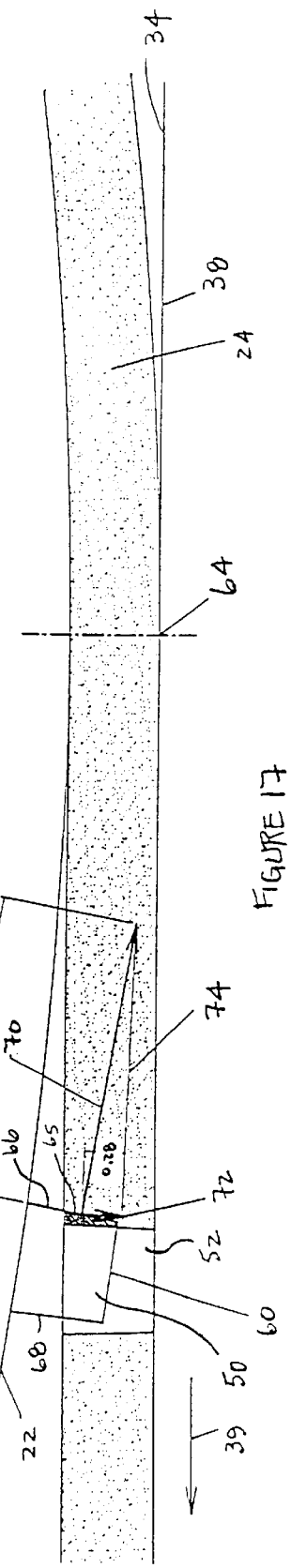
FIG. 17 is a side view of the apparatus of FIG. 15 wherein the forming nob has rotated to a point 8° beyond the normal line.

After removal of the excess fluff material, the pad 24 is conveyed from the forming drum 20 to a transfer surface 34. The transfer surface 34 may be formed by a cylindrical transfer roll 36 as shown in FIGS. 1 and 2. As shown in FIGS. 15–17 and discussed below, the transfer surface 34 may also be formed by a flat conveyor 38.

The forming drum 20 utilizes a vacuum source to deposit the fluff material on the forming screen 22 in the area of the forming chamber 26. In the transfer area 40 where the pad 24 is transferred from the forming drum 20 to the transfer surface 34, the forming drum 20 does not exert a vacuum. A pad blow-off air knife 42 is located near the transfer area 40. Both the lack of a forming drum vacuum and the air knife 42 assist in the transfer of the pad 24 to the transfer surface 34 in the transfer area 40.

In the illustrated apparatus, the cylindrical transfer roll 36 is a vacuum turn roll. The transfer surface 34 of the transfer roll 36 is a perforated surface and a vacuum source 43 is operatively associated with the transfer roll 36 whereby the transfer surface 34 pulls a vacuum at the transfer area 40. The use of a vacuum within the transfer roll 36 attracts the pad 24 to the transfer surface 34 and thereby assists in the transfer of the pad 24 to the transfer surface 34. A second air knife 44 is located within the transfer roll 36 to disengage the pad from the transfer roll 36. The transfer surface 34 does not exert a vacuum on the pad 24 in the area of the air knife 44.

In the apparatus illustrated in FIGS. 1 and 2, the pad 24 is deposited on a first tissue 46 as it leaves the vacuum area of the transfer roll 36 and is disengaged from the transfer roll 36. A second tissue 48 is subsequently deposited on the opposite surface of the pad 24. The tissues 46, 48 help to maintain the integrity of the pad 24 as it is later assembled into a product and placed in use. The use of such tissue layers with an absorbent pad is well known in the art. The use of such tissues 46, 48, however, is not required and the pad 24 may be assembled into a product without the use of such tissue layers. Alternative substrates, such as a layer of polymeric meltblown material, may also be used to enhance the integrity or cohesion of the pad 24.

It is also known to place a tissue layer on a forming roll and form a fluff pad directly on the tissue layer. When employing nobs 50 on a forming screen 22 in accordance with the present invention, however, a tissue layer is preferably not used on the forming screen. Such a tissue layer would be difficult to conform to the surface of both the forming screen 22 and the nobs 50 and the apertures 52 formed by the nobs 50 would most likely be deformed by the presence of such a tissue layer.

Following the placement of the tissues 46, 48 on opposite sides of the pad 24, the pad 24 is debulked. The pad 24 is compressed between two nip rolls to debulk the pad 24. Debulking the pad 24 reduces the thickness of the pad 24 and it may also slightly elongate the apertures 52 formed in the pad 24. The illustrated apparatus forms a continuous fluff pad which must be cut into individual pads in the manufacture of absorbent products. The outer lateral perimeter of the pad 24 illustrated in FIG. 3 may be defined by the outer lateral perimeter of the forming screen or by subsequently cutting the pad 24. A jet of water ejected at a high pressure and velocity or a die cutting operation may be used to efficiently cut the pad 24 to define its outer perimeter. It is also possible to deposit discrete individual pads on the forming screen 22 by segregating different portions of the forming screen 22 in a manner which is known in the art.

Figure 3:
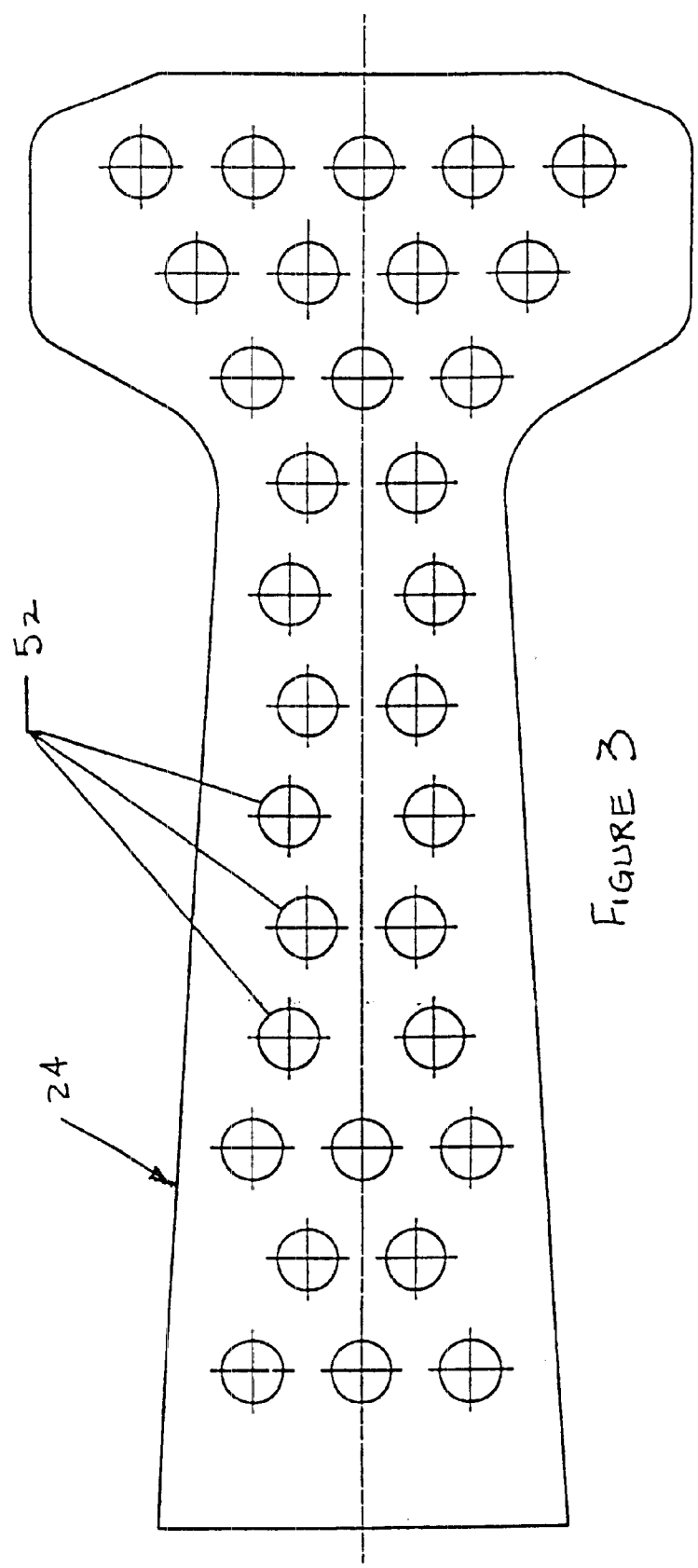
FIG. 3 is a top view of an apertured pad.

The apertures 52 are best seen in FIG. 3. In the illustrated embodiment, the apertures 52 extend through the entire thickness of the pad 24. It is also possible for the apertures 52 to extend only partially through the thickness of the pad 24.

The apertures 52 are formed by the nobs 50 located on the forming screen 22. Although not visible in FIGS. 1–2, nobs 50 are illustrated in FIGS. 4–19. The nobs 50 form an appendage or protusion on the forming screen 22. When the pad 24 is removed from the forming screen 22, the pad 24 has an aperture 52 or void space at the location where the pad 24 circumscribed the nob 50. By forming the apertures 52 in this manner, a subsequent cutting or calendering process is not required to form the apertures 52.

In the apparatus and method illustrated in FIGS. 1 and 2, the scarfing unit 28 is positioned to remove all of the fluff material which is disposed outwardly of the distal end 60 of the nob 50. The scarfing unit 28 thereby causes the nobs 50 to intersect the pad surface 25 disposed opposite the forming screen 22. The apertures 52 formed by the apparatus and method illustrated in FIGS. 1 and 2 therefore extend through the entire thickness of pad 24.

In alternative embodiments of the present invention, the apertures 52 formed in the surface 23 of the pad in contact with the forming screen 22 may not extend through the entire thickness of the pad 24. For example, if the configuration of the nobs 50 and of the scarfing unit 28 allowed the fluff material to not only circumscribe but also cover the distal end 60 of the nobs 50 when the fluff material was deposited on the forming screen, the apertures 52 would extend only partially through the thickness of the pad 24 and thereby take the form of a recess with an opening, i.e., aperture 52, in only one surface of the pad 24.

The nobs 50 may be formed out of a wide variety of different materials. For example, the nobs 50 may be formed out of plastic or metal materials. Metallic nobs are advantageous because they are durable and have a relatively low coefficient of friction. An aluminum nob provided with a Teflon (i.e., polytetrafluorethylene) release coating can be used to provide a durable and low friction nob. For example, a release coating found suitable for use with aluminum nobs was obtained under the tradename Hard Lube Coating from Pioneer Coating having offices in Green Bay, Wis. A nob 50 which has both durability and a low frictional coefficient may also be obtained by placing a Teflon coating on a steel body. Teflon coatings obtained under the tradename of either Norcoat-2 or Norcoat-3 from Pioneer Coating having offices in Green Bay, Wis. may be used to coat steel nobs.

Figure 18:
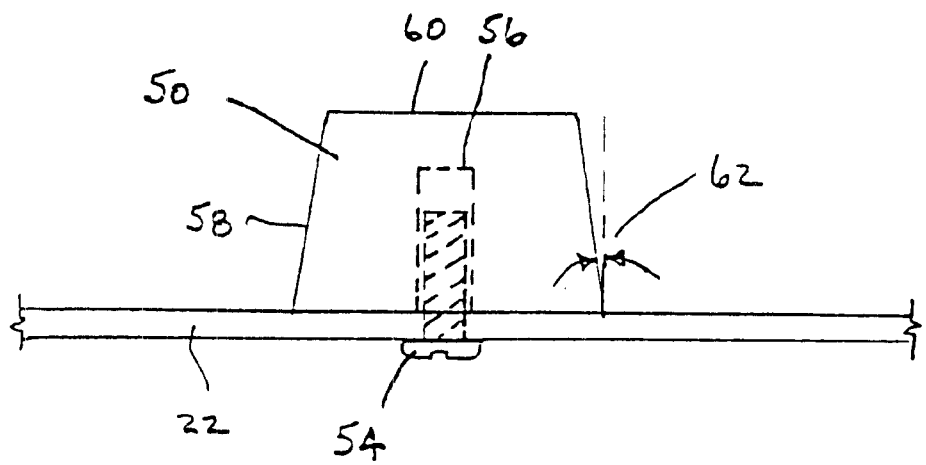
FIG. 18 is a side view of a nob.

The nobs 50 may be advantageously attached to the forming screen 22 by using threaded fasteners 54 inserted through the forming screen 22 and engaging a threaded bore 56 in the nob 50 as schematically shown in FIG. 18. Nobs may also be formed by including a protruding threaded shaft on the nob whereby the shaft may be threaded into an opening in the forming screen 22 or engaged by a nut on the opposite side of the forming screen 22.

The use of threaded fasteners 54 permit the nobs 50 to be conveniently attached, detached and reattached to the forming screen 22. When using such nobs, a first set of nobs may be relatively conveniently exchanged for a second set of nobs having a different size or geometric shape to alter the size and shape of the apertures in resulting pad. The use of threaded fasteners also permit individual nobs to be exchanged.

It is envisioned that the use of reattachable nobs on the forming screen 22 could also enable the nob positions to be reconfigured to alter the pattern of apertures 52 formed in the pad 24. The insertion of a threaded fastener through the forming screen 22, however, can damage the screen.

Nobs 50 may also be welded or otherwise permanently affixed to the forming screen 22. Less substantial materials and attachment methods can also be used to form and attach the nobs 50. For example, foam rubber nobs 50 adhered to a forming screen 22 with double sided tape have been successfully employed for limited production runs and may be removed or reconfigured without damaging the forming screen 22.

Figure 19:
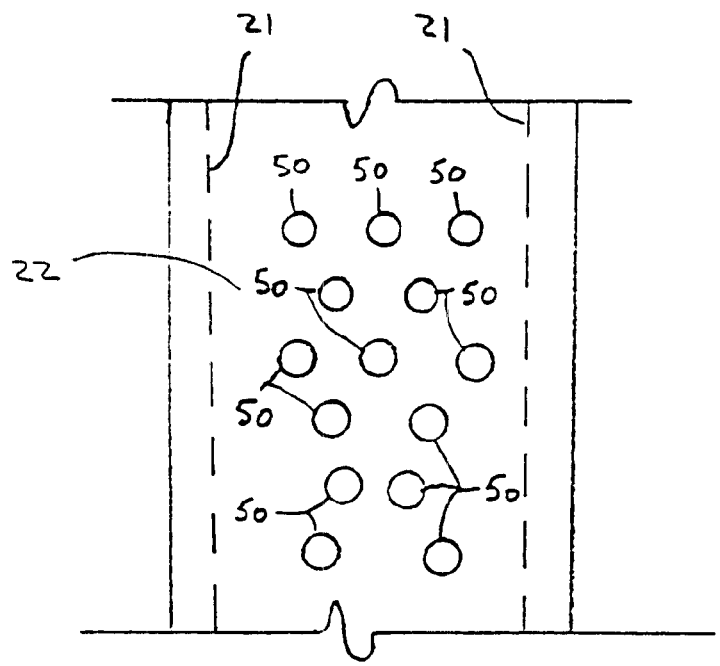
FIG. 19 is a top view of a forming screen and a plurality of nobs.

FIG. 19 illustrates a forming screen 22 with a plurality of nobs 50 attached thereto in a first pattern. Also shown in FIG. 19 are dashed lines 21 which designate the position where the outer lateral edges of the fluff pad 24 will be located after the fluff material has been deposited on the forming screen 22. As can be seen from FIG. 19, the nobs 50 lie within the interior region of the forming screen whereby the nobs 50 will be completely circumscribed by the fluff material deposited on the forming screen 22. In other words, if a projection similar to a nob 50 was positioned along the lateral edge of the forming screen 22 whereby it defined a portion of the lateral perimeter of the fluff pad 24 (and corresponded with dotted line 21) it would not be completely circumscribed or encircled by the deposited fluff material and would not define an aperture within the pad.

The illustrated nobs 50 do not include perforations or apertures on either the sidewalls or distal end of the nob 50 and, thus, process air is not pulled directly through the illustrated nobs 50. It would be possible, however, for the nobs to include such openings on the sidewall surface 58 to allow the process air to be removed therethough in addition to the remainder of the forming screen 22. If the apertures 52 did not extend completely through the thickness of the pad 24, it might be desirable for the distal end 60 of the nobs to include openings or for both the sidewall surface 58 and distal end 60 to include openings.

When nobs 50 without openings are employed on a forming screen 22, the total area of the forming surface which includes openings is reduced. For the pad 24 illustrated in FIG. 3 which is intended for use in a diaper, there are 32 apertures and the surface area of the apertures/nobs is approximately 15 percent of the total forming surface/pad surface area. An alternative configuration of nobs 50 which result in a pad similar to that shown in FIG. 3 but with only 16 apertures may also be used to produce an absorbent pad well-suited for use in a diaper.

Advantageously, the nob surface area may be between about 7 to about 15 percent, about 5 to about 25 percent, or less than about 50 percent of the total forming surface area. As used herein, the nob surface area is the cross sectional area of the nob at the base of the nob where the nob is attached to the forming screen and the total forming surface area includes the area of the forming screen on which the fluff material is deposited plus the nob surface area.

The nobs 50 may have a variety of different configurations. For example, the cross section of the nobs 50 may define a circle, oval, star, diamond, rectangle or any other geometric figure. Furthermore, the cross sectional shape of the nobs 50 may vary over the height of the nobs 50. For example, the nobs 50 may be provided with a slight taper whereby the distal end 60 of the nob 50 has an area which is less than the cross sectional area of the base of the nob at the point where the nob is attached to the forming screen 22. The inward taper of the sidewall 58 may advantageously be in the range of between 0° to about 15°. For example, sidewalls may advantageously have an inward taper of approximately 5° or 7°.

Alternatively, the sidewall surfaces 58 of the nob 50 may be perpendicular to the forming screen 22, pitched slightly outward, or vary over the perimeter or height of the nob 50. For example, a nob 50 could have a leading edge 68 which is perpendicular to the forming screen and a trailing edge 66 which is pitched slightly inward and thus have a pitch which varies over the perimeter of the nob 50. A nob 50 which is perpendicular near its base (i.e., has a 0° taper) but tapers inwardly near its distal end would have a pitch which varies over the height of the nob 50. Thus, the nobs 50 may take a variety of different shapes. The configuration of the nobs 50, however, must account for the interaction of the nob 50 and the pad 24 during the release of the pad 24 from the forming screen 22 which is described in greater detail below.

The nobs illustrated in FIGS. 4–18 have circular cross sections having a diameter of 1.91 cm (0.75 inch) at the base of the nob, a height of either 1.27 cm or 1.59 cm (0.5 or 0.625 inch) and a slight inward taper. As best seen in FIG. 18, the sidewall 58 has an inward inclination, illustrated by angle 62, of about 5° whereby the angle formed between the inward inclining sidewall 58 and the forming screen 22 is about 85°. Thus, the nob illustrated in FIG. 18 is a frustum (i.e., it defines a truncated cone).

For pads 24 intended for use with conventional absorbent products, the diameter or longest lateral dimension of the nobs 50 may be advantageously varied from between about 0.95 cm (0.375 inch) to about 5.08 cm (2 inches). The pattern formed by the nobs 50 on the forming screen 22 may be varied significantly. It is generally advantageous, however, to maintain a distance between each nob 50 which is at least as great as the greatest of the nob diameter (or longest lateral dimension of the nob 50) or the height of the nob 50.

An advantageous feature of the nobs 50 of the present invention is their ability to assist in the transfer of the pad 24 from the forming screen 22 to the transfer surface 34. This aspect of the nobs 50 is schematically illustrated in FIGS. 4–17.

FIGS. 4–11 and 12–14 illustrate the transfer of an apertured pad 24 from a cylindrical forming drum 20 to a cylindrical transfer roll 36. For purposes of clarity, a single nob 50 is illustrated in FIGS. 4–11 as it rotates and progressively releases the apertured pad 24. A normal line 64 which connects the centers of both the forming drum 20 and the transfer roll 36 is shown in FIGS. 4–11 and provides a common reference location in each of these Figures. The forming screen 22 and transfer surface 34 are respectively rotated about the centers of the forming drum 20 and transfer roll 36 in opposite rotational directions whereby the forming screen 22 and transfer surface 34 have a common direction of linear or tangential movement where they intersect the normal line 64. Thus, transfer surface 34 is moving in a direction which substantially corresponds to the movement of the pad 24 in the area near the normal line 64.

The point at which the forming screen 22 and transfer roll 36 are nearest one another lies along the normal line 64. In the transfer area near line 64, the fluff pad 24 has a first surface 23 in contact with the forming screen 22 and the moveable transfer surface 34 is positioned adjacent the opposite second surface 25 of the pad 24. At the point where the forming screen 22 and transfer surface 34 are closest, i.e., at their intersection with normal line 64, the forming screen 22 has a first tangential velocity (oriented perpendicular to the normal line 64) and the transfer surface has a second tangential velocity (oriented perpendicular to the normal line 64). The transfer surface 34 is engaged with the second surface 25 of the pad 24 at or near the normal line 64 in the transfer area 40.

A vacuum source 43 operatively associated with the transfer roll 36 attracts the pad 24 to the transfer surface 34. As the pad 24 moves with the transfer surface 34 it is released from contact with both the forming screen 22 and the nob 50. FIGS. 4–11 progressively illustrate this release of the pad 24 wherein the forming screen 22 is generally cylindrical and has a diameter which is greater than three times the magnitude of the diameter of the transfer surface 34 which is also generally cylindrical. Forming screens having a diameter of approximately 154.4 cm (60.8 inches) may be advantageously used with transfer surfaces 34 having a diameter of approximately 42.4 cm (16.7 inches) to provide a forming drum diameter/transfer surface diameter ratio of 3.6.

Advantageous configurations may also be obtained by utilizing a forming screen 22 having a radius which is twice or three times as great as the radius of the transfer surface 34. Alternative embodiments may also employ forming screens 22 which have a radius which is approximately equivalent to or smaller than the radius of the transfer surface 34. For example, the use of a flat transfer surface 34 can be considered the use of a transfer surface 34 having an infinite radius.

FIGS. 4–14 illustrate a forming drum 20 having a diameter of 154.4 cm and a transfer surface with a diameter of 42.4 cm; wherein the tangential velocity of the transfer surface 34 is equivalent to the tangential velocity of the forming screen 22; and nob 50 has a height of approximately 1.27 cm (0.5 inch).

FIG. 4 illustrates a representative nob 50 when it is centered on the normal line 64. FIG. 5 illustrates the point at which the nob 50 has rotated 0.75° (or 0.013 radians) about the center of the forming drum 20 past normal line 64. FIGS. 6–11 illustrate the nob 50 after it has respectively rotated 1.5°, 2.25°, 3°, 4.5°, 5.25° and 6° past normal line 64.

As can be seen in FIGS. 4–11, the trailing edge 66 of the nob 50 impinges upon the fluff pad 24 during the release of the pad 24 from the nob 50 and forming screen 22. That portion of the trailing edge of the nob 50 which impinges upon the pad 24 exerts a compressive force on the pad 24 and forms a thrust surface 65. The thrust surface 65 is located on the trailing edge 66 instead of the leading edge 68 of the nob 50 because of the relative tangential velocities of the forming screen 22 and transfer surface 34 in the transfer area 40 and the spatial configuration of the forming screen 22, nob 50 and transfer surface 34 in the transfer area 40.

The leading edge 68 of the nob 50 would impinge upon the pad 25 and exert compressive forces thereon if the transfer surface 34 had a relatively low velocity in comparison to the velocity of the forming screen 22. The spatial configuration of the forming screen 22, nob 50 and transfer surface 34 in the transfer area 40 will determine the precise point at which a relative increase in the velocity of the transfer surface 34 causes the trailing edge 66 of the nob 50 to exert a compressive force on the pad 24 instead of the leading edge 68 of the nob 50.

When employing a forming screen 22 and transfer surface 34 which are both generally cylindrical and wherein the radius of the transfer surface 34 is less than the radius of the forming screen 22, the trailing edge 66 of the nob 50 will generally impinge upon the fluff pad 24 when the transfer surface 34 has a tangential velocity which is at least as great as the tangential velocity of the forming screen in the transfer area. Further relative increases in the speed of the transfer surface 34 to 101, 102 or 103 percent of the velocity of the forming screen 22 in the transfer area 40 may also be advantageous. An excessive difference in the relative velocities of the transfer surface 34 and the forming screen 22, however, can cause damage to the pad 24 such as the stretching and cracking of the pad 24 during the release and transfer process.

In the embodiment illustrated in FIG. 1, the apparatus may be advantageously operated whereby the forming screen 22 has a tangential velocity of approximately 304.8 m/min (1,000 ft/min) and the transfer surface 34 has an approximately equivalent tangential velocity. Conventional forming screens are often operated at rates which produce tangential velocities within the range of approximately 91.4 m/min (300 ft/min) to 304.8 m/min (1,000 ft/min). The present invention may advantageously utilize a forming screen 22 operating within this velocity range but is not limited to this range of velocities.

FIGS. 12–14 are enlargements of the nob 50 in the same rotational positions shown respectively in FIGS. 6, 8 and 9. The compressive pressure exerted by the thrust surface 65 on the pad 24 can be denoted by a force vector 70 which represents the direction and magnitude of the total compressive pressure exerted by the thrust surface 65 located on the trailing edge 66 of the nob 50 against the pad 24. The actual compressive force 70 exerted by the thrust surface 65 will vary in magnitude as the nob 50 is withdrawn from the pad 24. That portion of the trailing edge 66 of the nob 50 which forms the thrust surface 65 will also change as the nob 50 is withdrawn from the pad 24.

The actual magnitude of the compressive force 70 will be dependent upon a number of variables, including not only the spatial configuration of the forming screen 22, nob 50 and transfer surface 34, but also the materials used to form the nob 50 and the pad 24. For example, the modulus of elasticity and Poisson's ratio of both the nob 50 and the pad 24 will affect the magnitude of the compressive force 70. As a general rule, denser pads will result in the nob exerting larger compressive forces. There will also be frictional forces existing between the nob 50 and the pad 24 which, when added to the compressive force 70, will result in a net force having a slightly different magnitude and orientation than the compressive force 70.

With regard to the spatial configuration of the apparatus, a taller nob will generally produce larger compressive forces than a shorter nob and a smaller diameter forming screen will generally produce larger compressive forces than a larger diameter forming screen. The determination of an exact magnitude for compressive force 70 can be quite complex. For the purposes of FIGS. 12–14, however, the magnitude of the compressive force 70 has been simplified and is represented at a constant value of 2.00 units of force.

The orientation of the compressive force 70 is more readily determined than the magnitude of the force 70. The direction of the compressive force 70 is primarily determined by the spatial configuration of the forming screen 22, nob 50 and transfer surface 34 and the relative motion of these apparatus components which determines the area and depth to which the nob 50 impinges upon the pad 24.

A variable which may affect the net force exerted by the nob 50 on the pad 24 is the frictional resistance between the pad 24 and the nob 50. Compressive force vectors 70 are illustrated in the Figures of the present application rather than the net force vectors. The orientation of the illustrated vectors 70 would substantially correspond to the orientation of the net force exerted by the nob 50 upon the pad 24 if the interface between the nob 50 and pad 24 is assumed to be frictionless. Such an assumption is reasonable for nobs 50 such as those illustrated in the Figures which have a friction-reducing coating and a slight-inward taper.

The compressive force 70 can be defined by two component vectors which are illustrated in FIGS. 12–14. One of the component vectors 72 is directed towards the transfer surface 34 and is normal to the transfer surface 34 at the location nearest the point on the thrust surface 65 corresponding to the origin of the compressive force 70. The second component vector 74 is at a right angle to the first component vector 72 and is oriented opposite to the direction of travel of the pad 24. When added together, vectors 72 and 74 are equivalent to compressive force vector 70. Because the first component vector 72 has an orientation which is normal to the transfer surface 34, it assists in the transfer of the pad 24 to the transfer surface 34.

The orientation of the compressive force 70 is determined, in part, by the shape and configuration of the nob 50. As the fluff is air-laid on the forming screen 22, it is subjected to a vacuum and thereby strongly attracted towards the forming screen 22. As the forming screen 22 rotates towards the transfer area 40, the fluff forming pad 24 is no longer subjected to a vacuum and expands slightly outwardly from the forming screen 22. During this expansion of the fluff material, the pad 24 also expands laterally to engage the sidewalls 58 of the nobs 50, if the fluff material did not already so engage the sidewalls 58 of the nobs 50. (The front portion of the sidewall 58 forms the leading edge 68 of the nob 50 while the rear portion of the sidewall 58 forms the trailing edge 66 of the nob 50.) Due to this expansion of the fluff material, beveling or undercutting the nob 50 would result in the fluff material expanding into the undercut space between the forming screen 22 and nob 50 when the vacuum is no longer attracting the fluff against the forming screen 22. Depending upon the angle of such a bevel or outward taper, some of the fluff material could become entrapped between the nob 50 and forming screen 22 during the release of the pad 24 and cause damage to the pad 24.

For these same reasons, the release of the pad 24 can be improved by providing a slight inward taper to the nob 50 whereby the nob 50 has a smaller cross sectional area at its distal end than at its base. The nobs 50 may advantageously have sidewalls 58 which have an inward inclination of about 5° or greater to aid in the release of the pad. By utilizing sidewalls 58 having an inclination which is approximately 5°, the apertures 52 formed by the nob 50 will have interior surfaces which do not diverge significantly from a perpendicular orientation to the outer surfaces of the pad 24 and still facilitate the release of the pad 24 as demonstrated in FIGS. 12–14.

As shown in FIG. 12 when the nob 50 has rotated 1.5° past the normal line 64, the first vector component 72 of the compressive force 70 comprises a relatively small portion of the total compressive force 70. In the illustrated configuration, and examining only the compressive force and not any frictional forces, the first vector component 72 has a magnitude of 0.33 units of force for every 2.0 units of total compressive force 70. FIG. 13 illustrates the point at which the nob 50 has rotated 30 past the normal line 64. At this point, the first vector component 72 has a magnitude of 0.57 units for every 2.0 units of total compressive force 70. FIG. 14 illustrates the point at which the nob 50 has rotated 4.5° past the normal line 64. At this point, the first vector component 72 has a magnitude of 0.79 units for every 2.0 units of total compressive force 70.

Thus, in the configuration illustrated in FIGS. 12–14, the percentage of the total compressive force 70 which is directed normal to the transfer surface 34 increases as the nob 50 releases the pad 24. It can also be seen from FIGS. 12–14 that the total area of the thrust surface 65 progressively decreases as the nob 50 releases the pad 24 and that the extent of impingement by the thrust surface 65 upon the pad 24 progressively increases as the pad 24 is released.

FIGS. 15–17 illustrate the transfer of an apertured pad from a cylindrical forming screen 22 to a flat conveyor 38. The transfer surface 34 of the flat conveyor 38 may be operatively associated with a vacuum source whereby a vacuum is used to attract the pad 24 to the flat conveyor 38 and assist the transfer.

The transfer of the pad 24 to a flat transfer surface 34 can also be assisted by the trailing edge 68 of the nobs 50 imparting a compressive force on the pad 34 in the same manner as that described above for the transfer of a pad 24 to a cylindrical transfer surface 34. When the transfer is to a flat transfer surface 34, however, the relative velocity of the transfer surface 34 will have to be increased relative to the velocity of the forming screen to ensure that it is the trailing 66, rather than the leading 68 edge of the nob 50 which impinges upon the pad 24.

The forming screen 22 and nob 50 illustrated in FIGS. 15–17 are similar to those illustrated in FIGS. 12–14. FIGS. 15–17, however, depict a flat transfer surface 34 wherein the transfer surface 34 of the flat conveyor 38 has a velocity which is 103 percent of the velocity of the forming screen 22. Arrow 39 indicates the direction of travel of the flat conveyor 38.

For the apparatus illustrated in FIGS. 15–17, when the velocity of the flat transfer surface 34 is equivalent to the velocity of the forming screen 22, the leading edge 68 of the nob 50 will impinge upon the pad 34. When the flat transfer surface 34 has a velocity which is 101 percent of the velocity of the forming screen 22, the nob 50 will impinge upon the pad 34 with both the leading edge 68 and trailing edge 66 and at approximately equal magnitudes at different points during the release process. When the velocity of the flat transfer surface 34 has been relatively increased to 102 percent of the velocity of the forming screen 22, however, it will be the trailing edge 66 of the nob 50 which will primarily impinge upon the pad 34 and the nob 50 will thereby assist in the transfer of the pad 24 to the flat transfer surface 34. If the velocity of the flat transfer surface 34 exceeds 103 percent of the velocity of the forming screen surface, i.e., it has a draw of more than 103 percent, a pad 24 formed primarily out of cellulosic fluff material may be damaged by stretching or cracking.

For the embodiment illustrated in FIGS. 15–17, when the forming screen 22 has a velocity of approximately 304.8 m/min (1,000 ft/min) and the flat transfer surface 34 has a velocity of approximately 102 to 103 percent of the forming screen velocity, the trailing edge 66 of the nob 50 will impinge upon the pad 24 and a pad 24 formed out of cellulosic fluff material will be unlikely to experience stretching or cracking due to the differential in velocities.

It is noted that a particular relative difference in the tangential velocity of the forming screen 22 and the transfer surface 34 corresponds to a particular relative difference in the tangential linear advancement of the forming screen 22 and transfer surface 34 regardless of the absolute velocity of the forming screen 22 and transfer surface 34. For example, if the transfer surface 34 has a velocity of 101 percent of the forming screen 22, the transfer surface 34 will advance 101 cm for every 100 cm the forming screen 22 advances, regardless of their absolute velocities.

While this invention has been described in detail, it will be readily apparent to a person of ordinary skill in the art that various changes and modifications can be made without departing from the spirit and general principles of the invention. All of such changes and modifications are contemplated as being within the scope of the present invention as defined by the subjoined claims. Furthermore, this application is intended to cover such departures from the present disclosure as come within known or customary practice in the art.

What is claimed is:

1. An apparatus for manufacturing a pad, said apparatus comprising:
    a rotatable forming screen, said forming screen having a generally cylindrical surface and at least one outwardly projecting nob, said at least one outwardly projecting nob interiorly positioned on said forming screen whereby said forming screen circumscribes said nob, said forming screen being rotatable at a rate defining a first tangential velocity;
    a material source positioned adjacent said forming screen whereby a material layer is depositable on said forming screen and said at least one nob is circumscribable by the material layer, the material layer thereby forming the pad and having a first surface disposed in contact with said forming screen and a second surface disposed opposite said first layer;
    a moveable transfer surface, said transfer surface being engageable with the second surface of the material layer, said transfer surface being moveable in a direction substantially corresponding to the movement of the engageable material layer and at a second velocity, said second velocity being at least as great as said first velocity;
    a means for attracting the material layer to said transfer surface; and
    a thrust surface disposed on a trailing edge of said at least one nob, said thrust surface imparting a compressive force on the engageable material layer as said forming screen and said transfer surface respectively move at said first and second velocities, said compressive force including a component vector directed towards said transfer surface.

2. The apparatus of claim 1 wherein said transfer surface is a substantially flat surface.

3. The apparatus of claim 2 wherein said second velocity is greater than said first velocity.

4. The apparatus of claim 2 wherein said second velocity is at least about 102 percent of said first velocity.

5. The apparatus of claim 2 wherein said second velocity is at least about 103 percent of said first velocity.

6. The apparatus of claim 1 wherein said transfer surface is a substantially cylindrical surface.

7. The apparatus of claim 1 wherein said forming screen includes a plurality of outwardly projecting nobs interiorly positioned on said forming screen whereby said forming screen circumscribes each of said plurality of nobs.

8. The apparatus of claim 1 wherein said at least one nob is reattachable on said forming screen.

9. The apparatus of claim 8 further comprising a threaded fastener securing said at least one nob.

10. The apparatus of claim 1 wherein said at least one nob has a distal end and side walls extending from said forming screen to said distal end, said nob having a first cross sectional area at said forming screen and second cross sectional area at said distal end, at a portion of said side walls having an inward inclination of at least about 5 degrees.

11. The apparatus of claim 10 wherein said at least one nob is a frustum.

12. The apparatus of claim 1 further comprising a scarfing device, said scarfing device positioned to remove excess material disposed outwardly of a distal end of said at least one nob.

13. The apparatus of claim 1 wherein said means for attracting the material layer comprises a vacuum source disposed in operative communication with said transfer surface.

14. An apparatus for manufacturing a pad, said apparatus comprising:
    a rotatable forming screen, said forming screen defining a first generally cylindrical surface with a first radius and having at least one outwardly projecting nob, said at least one outwardly projecting nob interiorly positioned on said forming screen whereby said forming screen circumscribes said nob, said forming screen being rotatable at a rate defining a first tangential velocity;
    a material source positioned adjacent said forming screen whereby a material layer is air layable on said forming screen and said at least one nob is circumscribable by the material layer, the material layer thereby forming a pad and having a first surface disposed in contact with said forming screen and a second surface disposed opposite said first layer;
    a rotatable transfer surface, said transfer surface defining a second generally cylindrical surface with a second radius, said transfer surface being engageable with the second surface of the material layer, said transfer surface and said forming screen having opposed rotatable directions, said transfer surface being movable at a second tangential velocity, said second velocity being greater than said first velocity;

a vacuum source disposed in operative communication with said transfer surface whereby said material layer is attractable to said transfer surface; and a thrust surface disposed on a trailing edge of said at least one nob, said thrust surface imparting a compressive force on the engageable material layer as said forming screen and said transfer surface respectively move at said first and second velocities, said compressive force including a component vector directed towards said transfer surface.

15. The apparatus of claim 14 wherein said first radius is substantially equivalent to said second radius.

16. The apparatus of claim 14 wherein said first radius is larger than said second radius.

17. The apparatus of claim 14 wherein said second velocity is greater than said first velocity.

18. The apparatus of claim 14 wherein said second velocity is at least about 101 percent of said first velocity.

19. The apparatus of claim 14 wherein said second velocity is at least about 102 percent of said first velocity.

20. The apparatus of claim 14 wherein said second velocity is at least about 103 percent of said first velocity.

21. The apparatus of claim 14 wherein said forming screen includes a plurality of outwardly projecting nobs interiorly positioned on said forming screen whereby said forming screen circumscribes each of said plurality of nobs.

22. The apparatus of claim 14 wherein said at least one nob is reattachable on said forming screen.

23. The apparatus of claim 22 further comprising a threaded fastener securing said at least one nob.

24. The apparatus of claim 14 wherein said at least one nob has a distal end and side walls extending from said forming screen to said distal end, said nob having a first cross sectional area at said forming screen and second cross sectional area at said distal end, a portion of said side walls having an inward inclination of at least about 5 degrees.

25. The apparatus of claim 24 wherein said at least one nob is a frustum.

26. The apparatus of claim 14 further comprising a scarfing device, said scarfing device positioned to remove excess material disposed outwardly of a distal end of said at least one nob.

* * * * *